United States Patent [19]
Shelton et al.

[11] Patent Number: 5,601,582
[45] Date of Patent: Feb. 11, 1997

[54] CUTTING CATHETER

[75] Inventors: Susan C. Shelton, Ararat, N.C.; Neal E. Fearnot, West Lafayette; Thomas A. Osborne, Bloomington, both of Ind.

[73] Assignees: Wilson-Cook Medical Inc., Winston-Salem, N.C.; MED Institute Inc., W. Lafayette; Cook Inc., Bloomington, both of Ind.

[21] Appl. No.: 340,565

[22] Filed: Nov. 16, 1994

[51] Int. Cl.$^6$ .......................... A61B 17/32; A61B 17/20
[52] U.S. Cl. ................................. 606/170; 604/22
[58] Field of Search .................... 606/167–170, 606/191–194, 205–207, 127; 604/95, 170, 22, 27; 623/12; 128/772

[56] References Cited

U.S. PATENT DOCUMENTS

| | | | |
|---|---|---|---|
| 4,445,509 | 5/1984 | Auth | 606/159 |
| 4,681,106 | 7/1987 | Kensey et al. | 604/22 X |
| 4,886,061 | 12/1989 | Fischell et al. | 606/159 |
| 4,922,902 | 5/1990 | Wuchinich et al. | 606/22 |
| 4,922,905 | 5/1990 | Strecker | 623/12 X |
| 5,254,130 | 10/1993 | Poncet et al. | 606/170 X |
| 5,308,324 | 5/1994 | Hammerslag et al. | 606/191 |
| 5,486,183 | 1/1996 | Middleman et al. | 606/127 |
| 5,509,923 | 4/1996 | Middleman et al. | 606/170 X |

*Primary Examiner*—Michael Powell Buiz
*Assistant Examiner*—Nancy Connolly Mulcare
*Attorney, Agent, or Firm*—Richard J. Godlewski

[57] ABSTRACT

A papillotome (10) including a multi-lumen inner member tube (11) with an outer member tube (16) positioned around the proximal portion thereof with a spacing therebetween for limiting the radial expansion of the inner member tube so that the elastic limit of the inner member tube is not exceeded. The material of and the spacing between the inner and outer member tubes is selected so as to longitudinally distribute the radial expansion of the inner member tube from a fixed or partial attachment of the inner and outer member tubes.

21 Claims, 6 Drawing Sheets

CUTTING CATHETER

TECHNICAL FIELD

This invention relates generally to medical catheters and, in particular, to a cutting catheter also known as a papillotome.

BACKGROUND OF THE INVENTION

Cutting catheters, commonly known as papillotomes, are utilized for a variety of surgical procedures for cutting tissue and, more particularly, severing papilla at a number of different anatomical sites. One particular surgical procedure involves positioning an endoscope through the esophagus, stomach, and duodenum of a patient and positioning the tip thereof at the papilla of Vater. The common duct secretes liver bile into the duodenum and digestive tract at the papilla of Vater. Secretions and mineral deposits form calculi in the common duct and can cause an interruption of liver bile flow into the duodenum. In addition, the calculi can irritate the tissue surrounding the papilla of Vater and cause further blockage of liver bile. A papillotome is typically inserted through the endoscope into the papilla of Vater to enlarge the duct opening. This permits calculi to pass therethrough into the duodenum and clear the duct opening for resumed liver bile flow.

The papillotome utilized for this procedure is commonly 200 cm long with an electrically conductive cutting wire extending through a multi-lumen 6 French catheter. One lumen of the catheter is utilized for passing the electrically conductive cutting wire therethrough. Another lumen of the catheter is typically utilized for extending a wire guide therethrough and positioning the papillotome at the proper anatomical site through the endoscope. The proximal end of the papillotome typically includes a manually operated handle attached to the cutting wire so as to deflect the distal end of the catheter. This is done to form a loop at the distal end of the cutting catheter to engage tissue and, more particularly, papilla. In addition, the deflection of the catheter tip is used to position the cutting wire, such as in the papilla of Vater for enlarging the opening thereat.

One problem associated with this particular papillotome construction is the proximal connection of the multi-lumen catheter to the handle. As the handle is operated, the cutting wire causes compression of the multi-lumen catheter and concentrates the stress at the connection of the multi-lumen catheter and the handle. As a result, longitudinal compression of the multi-lumen catheter at the handle connection causes radial expansion of the plastic material beyond its elastic limit. Further compression of the multi-lumen catheter results in twisting and inelastic deformation of the catheter tube. A further consequence of this inelastic deformation is rupturing and tearing of the multi-lumen catheter wall near the connection of the catheter to the handle. This presents an electrical hazard to the patient as well as the attending physician.

Attempts to correct this inelastic deformation problem have included reinforcing the connection of the catheter to the handle with, for example, an outer reinforcing tube tightly positioned around the proximal end of the catheter tube and the distal end of the handle. Unfortunately, this has merely transferred the concentration of stress distally away from the catheter and handle connection. As a result, the multi-lumen catheter again inelastically deforms, ruptures and tears just distal of the reinforcement. Reinforcement of the entire catheter length is usually not possible since the endoscope limits the diameter of the multi-lumen catheter. The selection of stiffer materials has also been unsatisfactory due to the fact that the papillotome is extremely long and needs to be flexible for its tortuous journey.

SUMMARY OF THE INVENTION

The foregoing problems are solved and a technical advance is achieved in an illustrative cutting instrument of the present invention in which an outer elongated member tube is positioned around the proximal portion of an inner elongated member tube through which a compression member wire passes. In particular, the outer elongated member tube has a passage extending therethrough with a cross-sectional area in which the inner member tube can radially expand no greater than its elastic limit. As a result, the radial expansion of the inner member tube in the outer member passage is distributed longitudinally from any fixed or partial attachment of the compression member wire or outer member to the inner member tube before the elastic limit of the inner member tube is reached.

The inner elongated member tube of the cutting catheter includes an elastic material, preferably polytetrafluoroethylene, with its lubricious quality for easy insertion through an endoscope to an anatomical site. However, the elastic material can include at least one from a group consisting of polyfluoroethylenepropylene, polyimide, polyamide, polypropylene, polyurethane, polyethylene, and polyethyletheralate. Similarly, the outer member tube preferably includes a polytetrafluoroethylene material; however, the outer member tube can include at least one material from a group consisting of vinyl, polyvinylchloride, polyimide, polypropylene, polyethylene. The outer member tube can also include a metallic alloy of, for example, stainless steel, platinum, gold, or any other biocompatible metal. Alternatively, the tube can comprise a tightly wound coil or braid in which the inner passage thereof maintains its cross-sectional area and its spacing with the inner member tube to limit radial expansion of the inner member tube. The selection of material for the inner and outer member tubes varies the spacing therebetween; however, the spacing must be maintained so as to limit the radial expansion of the inner member tube to no greater than the elastic limit thereof.

In the preferred embodiment, the inner member tube includes a first passage in which the compression member wire passes therethrough. A second passage is also provided and in communication with a side hub for advantageously passing a wire guide therethrough. A heat shrink tube positions the side hub and the outer member tube relative to each other. However, the cross-sectional area and spacing between the inner and outer member tubes is maintained to allow radial expansion of the inner member between the inner and outer member tubes without exceeding the elastic limit of the inner member tube.

A heat shrink tube is also positioned around the proximal end of the outer member tube and the distal end of a handle positioned thereat. This advantageously fixes the relative position of the outer member tube with respect to the proximal portion of the inner member tube and the compression member cutting wire.

The cutting catheter also includes a two-part handle of which one part is connected to the compression member wire and the other is connected to the inner member tube. The connection of one handle part and inner member tube advantageously includes a cannula positioned in one passage of the tube of which the compression member wire passes

DETAILED DESCRIPTION

Figure 1:
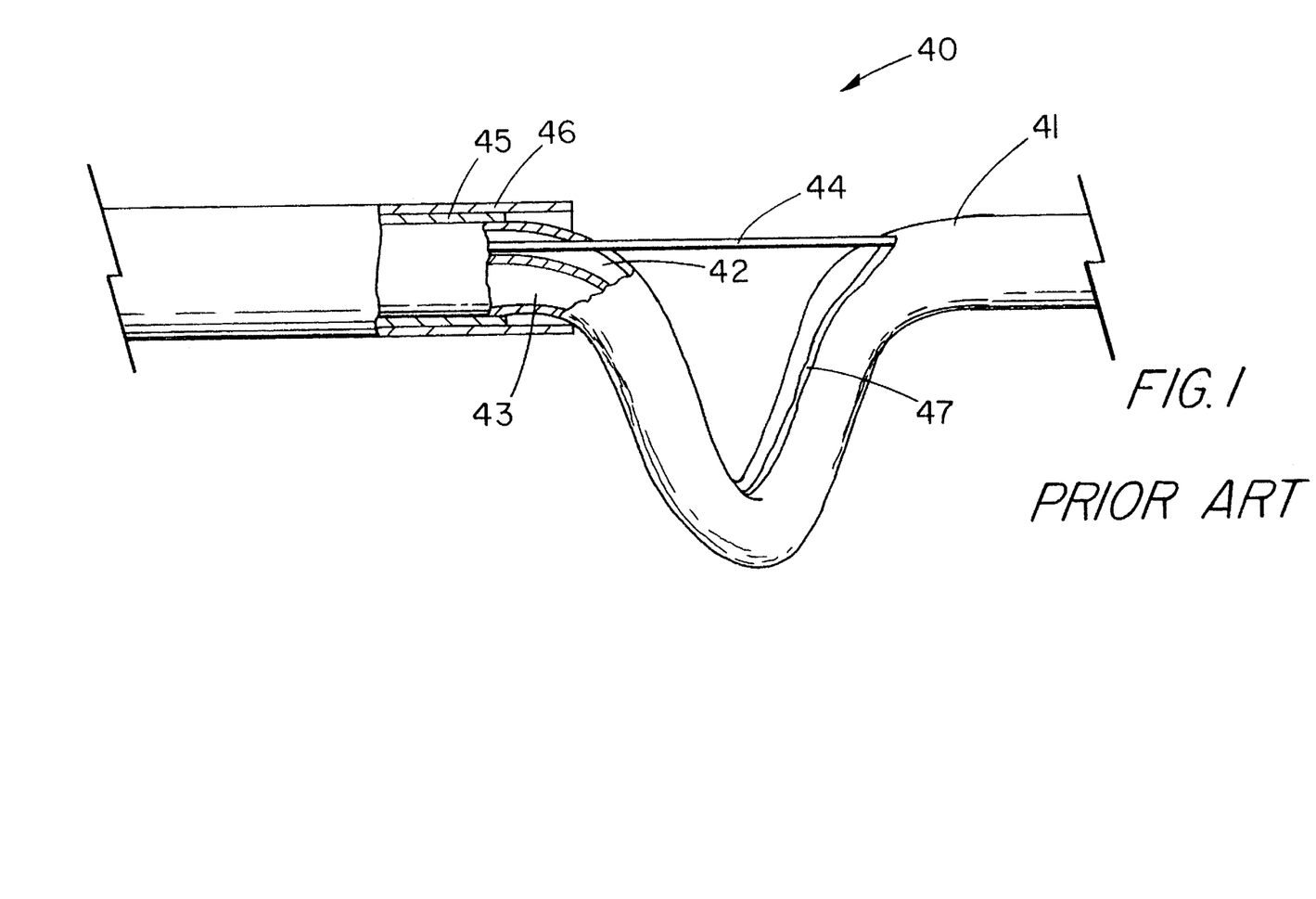
FIG. 1 depicts a prior art papillotome.

FIG. 1 depicts prior art papillotome 40 with inner member tube 41 having passages 42 and 43 extending longitudinally therethrough, with compression member 44, such as an electrically conductive wire, extending through inner member passage 42. Intermediate and outer heat shrink tubes 45 and 46 are tightly positioned around the proximal portion of inner member tube 41 to reinforce and prevent the inner member tube from twisting and rupturing when compression member 44 is pulled to fold back the distal end of the inner member. However, as depicted, the intermediate and outer heat shrink tubes have simply moved the high concentration of stress, which is normally experienced at the interconnection of the inner member tube and catheter handle, longitudinally along the inner member just distal of the heat shrink tubes. As a result, when compression member 44 is actuated, inner member tube 41 is radially expanded beyond its elastic limit and twists just distal of heat shrink tubes 45 and 46. The inelastic deformation and twisting of inner member tube 41 with compression member 44 extending therethrough commonly causes the wall of inner member passage 42 to rupture and externally expose compression member 44 through tear 47. As a consequence, the loop at the distal end of the inner member cannot be properly controlled and, more importantly, externally exposed, electrically conductive compression member 44 presents a clear safety hazard to the patient as well as the attending physician.

Figure 2:
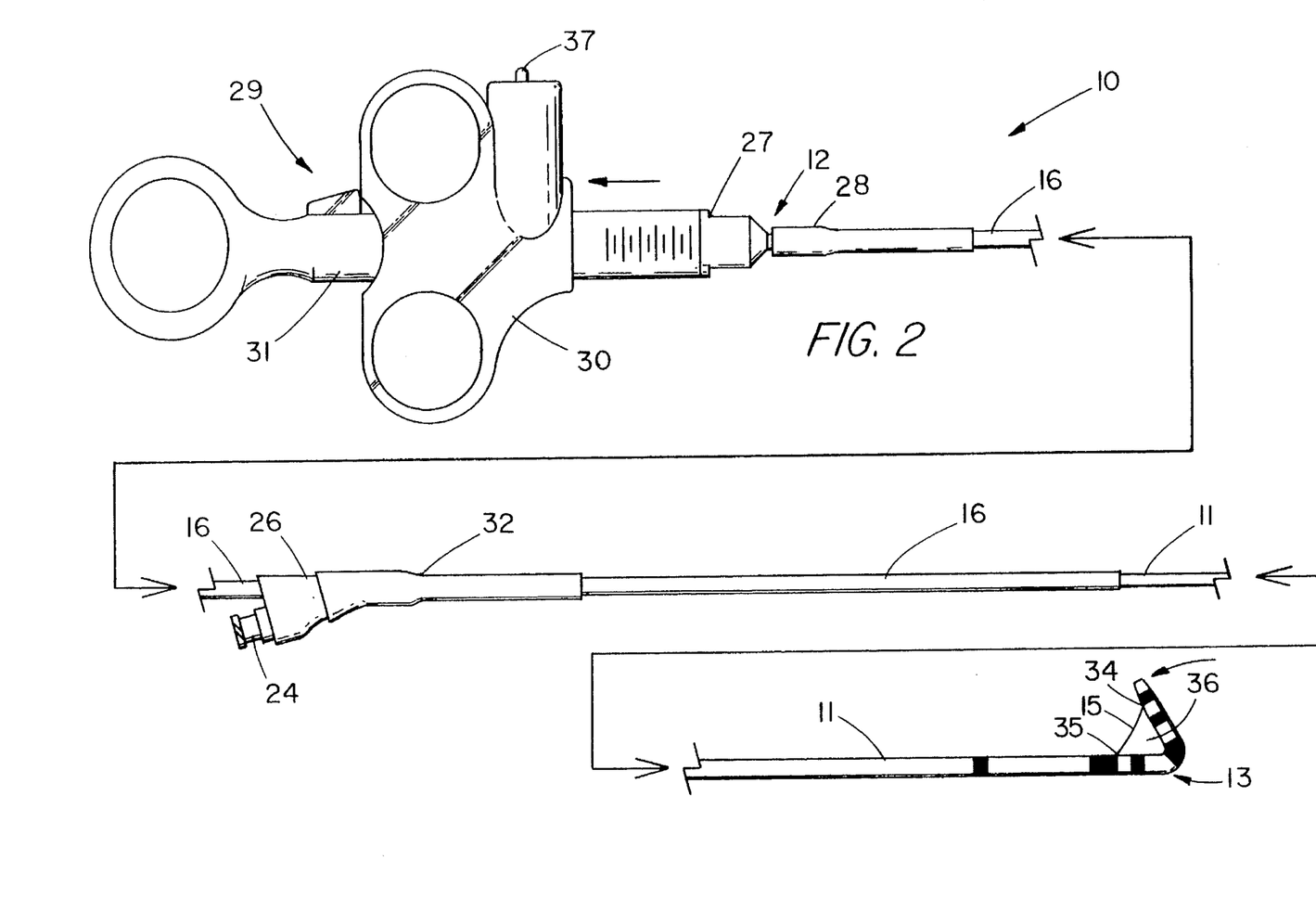
FIG. 2 depicts a preferred embodiment of an illustrative cutting catheter of the present invention, also known as a papillotome.

FIG. 2 depicts a preferred embodiment of an illustrative cutting catheter 10, also known as a papillotome, for cutting tissue or, more particularly, severing papilla with electrically energizable compression member 15 externally positioned about distal end 13 of inner elongated member 11. The compression member, normally comprising a metallic, electrically conductive wire, tube, cannula, or braid, is internally anchored in a passage of inner member 11 at distal end 13 and externally exits the inner member for a short distance via distal side ports 34 and 35. The compression member extends almost the entire length of the inner member passage and is attached to manually operated, three-ring catheter handle 29. As shown, the catheter handle is in a selected, actuated position in which handle part 30 has been pulled proximally with respect to handle part 31. Since the proximal end of the compression member is attached to actuated handle part 30, the distal end of the inner member is folded back upon itself, forming distal loop 36 with externally positioned compression member 15. Tissue is commonly electrosurgically severed with the externally positioned compression member. More particularly, papilla are inserted into distal loop 36 and severed with electrically energized compression member 15. Electrical energy is commonly applied to the compression member via electrical terminal 37 positioned on catheter handle 29.

Figure 5:
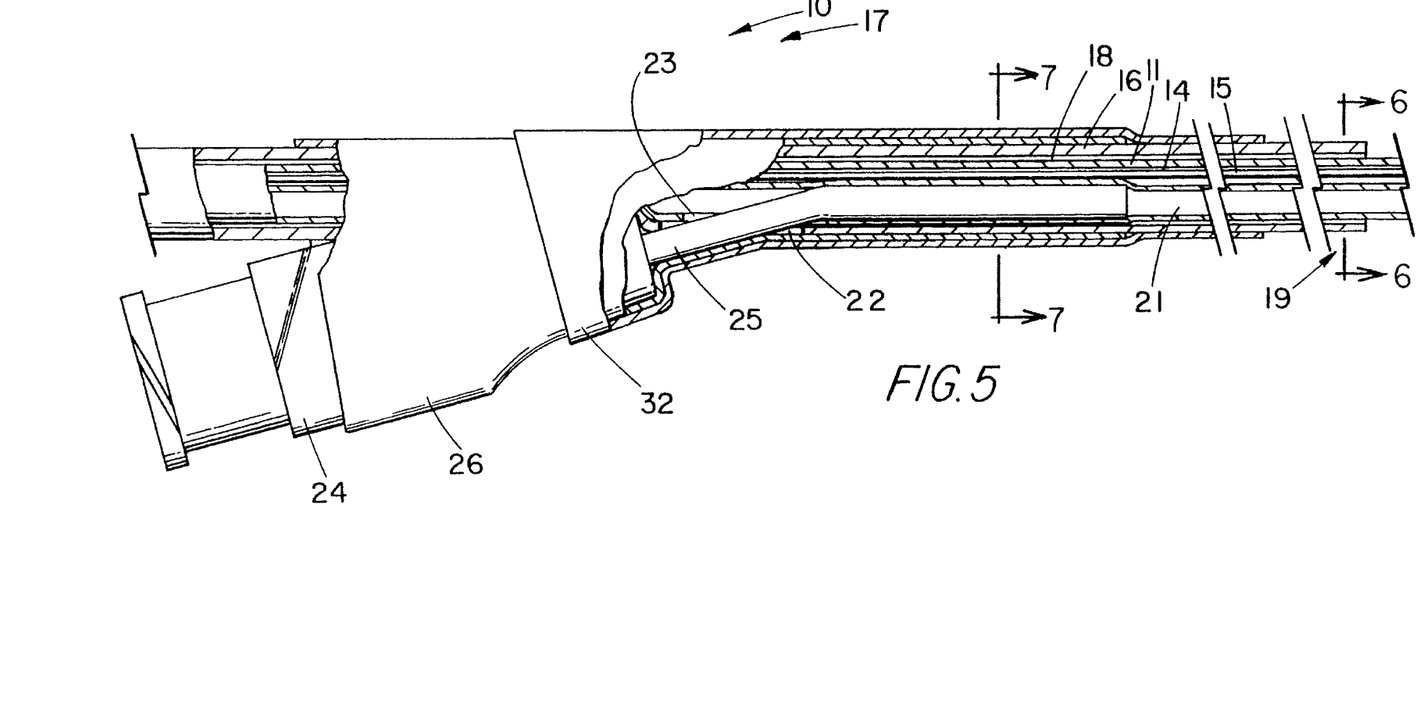
FIG. 5 depicts an enlarged, partially cross-sectioned view of the cutting catheter of FIG. 2 about the proximal portion of the inner member with a side hub communicating with a second passage of the inner member.

FIG. 5 depicts an enlarged, partially cross-sectioned view of cutting catheter 10 of FIG. 2 about proximal portion 17 of inner member 11 with side hub 24 communicating with second passage 21 of the inner member via cannula 25 positioned therein. Outer member 16 is coaxially positioned around inner member 11 with inner passage 18 of the outer member providing a spacing between the two members. This spacing between the two members allows inner member 11 to radially expand within its elastic limit and longitudinally distribute the radial expansion distally along the inner member when compression member 15 is selectively actuated by catheter handle 29.

Figure 9:
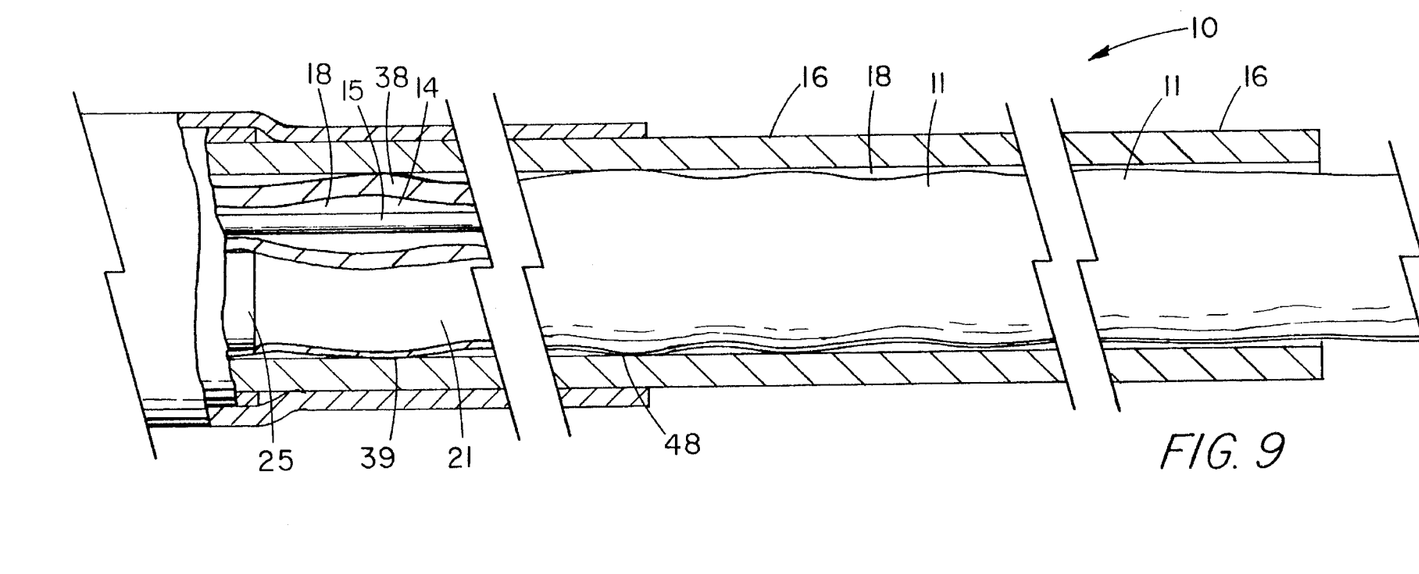
FIG. 9 depicts an enlarged, partially cross-sectioned view of the cutting catheter of FIG. 5 with the outer member longitudinally distributing the radial expansion of the inner member.

FIG. 9 depicts an enlarged, partially cross-sectioned view of cutting catheter 10 of FIG. 5 with outer member 16 longitudinally distributing the radial expansion of inner member 11. As a result, the inelastic deformation and twisting of inner member 11 is eliminated along with the rupture and tearing of first inner member passage wall 38 distal of the attachment of the compression member to the inner member, as well as the attachment of inner member 11 to outer member 16 at cannula 25. As compression member 15 is proximally pulled through first passage 14 of inner member 11, the inner member is longitudinally compressed and starts to radially expand adjacent to a point of attachment, such as due to cannula 25 being positioned in second inner member passage 21 via side ports in the inner and outer member tubes. By way of example, initial radial expansion of inner member 11 causes contact with outer member 16 at contact point 39. The diameter of outer member passage 18 is selected to be larger than the outside diameter of inner member 11. The spacing between the inner and outer members is sufficient to allow radial expansion of the inner member that is no greater than the elastic limit of the inner member. When the inner member makes contact at contact point 39, the expansion force is directed longitudinally down the inner member and, in this case, at least distally from the initial contact point. The inner member will continue to radially expand distally from the initial contact point until the inner member makes contact at second contact point 48. This longitudinal distribution of the radial expansion of the inner member is continued until the compression force exerted by compression member 15 is totally dissipated. The length of outer member 16 is selected so that the radial expansion and the longitudinal distribution of the inner member is maintained within the passage of the outer member.

As depicted, the longitudinal distribution of the expansion force creates a wave-like or rippling of the outer surface of inner member 11 within passage 18 of outer member 16. Since the radial expansion of the inner member is confined so as not to exceed the elastic limit of the inner member, twisting and rupturing of the inner member is advantageously eliminated. Although the distal most point of attachment between the inner and outer members is at the positioning of cannula hub 25 in passage 21 of the inner member, the compressive force of compression member 15 is also applied to the proximal attachment of the inner member to catheter handle 29. However, since the spacing between the inner and outer members is maintained along the entire length of the outer member, any radial expansion of the inner member will be confined within passage 18 of outer member 16 and longitudinally distributed along the inner member from the point of attachment.

Figure 3:
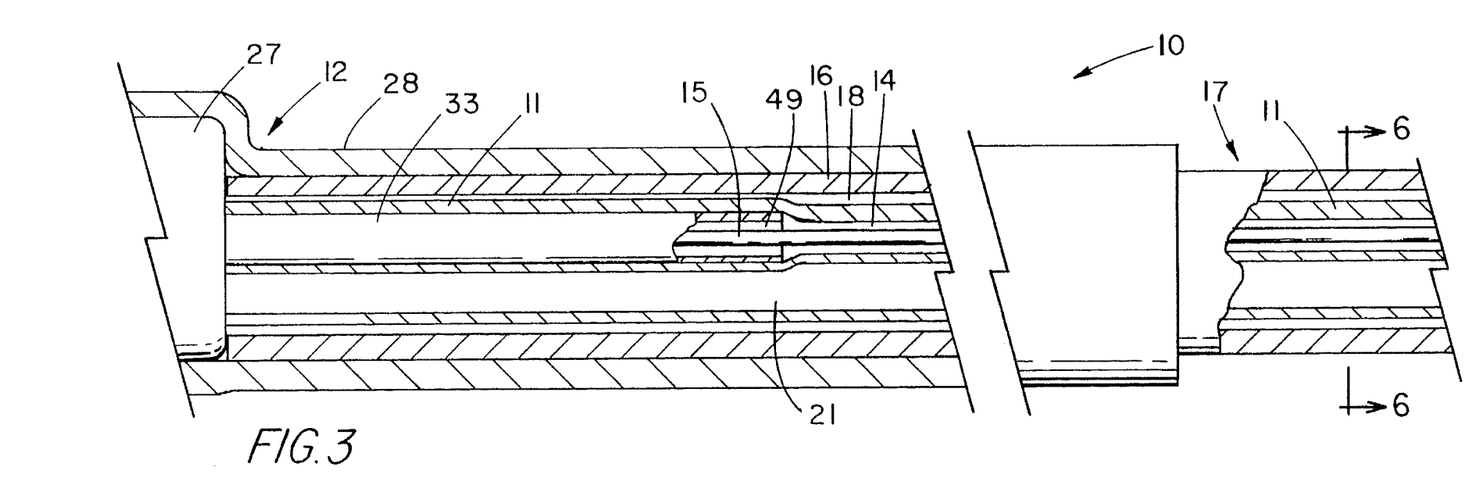
FIG. 3 depicts an enlarged, partially cross-sectioned view of the cutting catheter of FIG. 2 proximate the interconnection of the inner member and the catheter handle hub.

FIG. 3 depicts an enlarged, partially cross-sectioned view of cutting catheter 10 of FIG. 2 proximate the interconnection of inner member 11 and catheter handle hub 27. Inner elongated member 11 comprises a 6 French bi-lumen polytetrafluoroethylene material tube with a durometer of 50 to 65 on the Shore D hardness scale. Bi-lumen inner member tube 11 is approximately 200 cm in length with an outside diameter of approximately 0.083 inches. Inner member tube 11 includes first passage 14 with a diameter of approximately 0.022 inches and a second, adjacent passage 21 with a larger diameter of approximately 0.041 inches, both extending longitudinally therethrough. The minimum outer wall thickness of the inner member tube is approximately 0.005 inches, and the minimum thickness of the wall between inner member passages 14 and 21 is approximately 0.006 inches.

Figure 6:
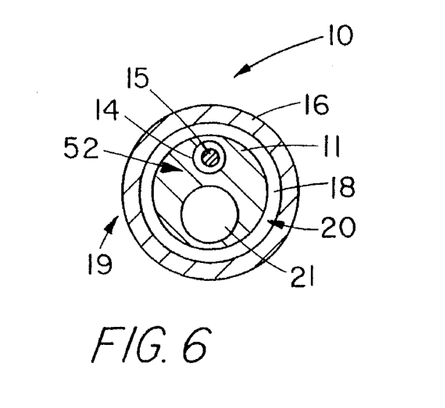
FIG. 6 depicts a cross-sectional view of the cutting catheter of FIG. 3 taken along the line 6—6.

FIG. 6 depicts a cross-sectional view of cutting catheter 10 of FIG. 3 taken along the line 6—6. Bi-lumen inner member tube 11 is coaxially positioned in inner passage 18 of outer member tube 16. Cross-sectional area 20 of outer member passage 18 is greater than cross-sectional area 52 of inner member tube 11. The spacing between the inner and outer member tubes is selected based on the inner member material, so that the inner member material can radially expand, but no greater than the elastic limit thereof. The spacial relationship of first inner member passage 14 and second inner member passage 21 is also shown. Compression member 15 is positioned in first inner member passage 14.

Returning the reader's attention to FIG. 3, outer member 16 preferably comprises a 10 French single lumen polytetrafluoroethylene material tube with a durometer of 50 to 65 on the Shore D hardness scale. Single lumen outer member tube 16 is approximately 21 cm in length with an outside diameter of approximately 0.131 inches. Outer member tube 16 includes inner passage 18 with an inside diameter of approximately 0.097 inches. The proximal ends of inner member tube 11 and outer member tube 16 coaxially abut catheter handle hub 27. Catheter handle hub 27 includes a cannula 33 extending longitudinally into first inner member passage 14 for approximately 18 mm. Cannula 33 comprises a 20 gauge stainless steel tube approximately 2.5 cm in length with an outside diameter of approximately 0.035 inches and an inside diameter of approximately 0.023 inches. Outer member tube 16 is held in position next to catheter handle hub 27 with a 3.5 cm length of commercially available polyolefin material heat shrink tube 28 positioned around and heat shrunk thereto. Compression member 15 extends longitudinally through first inner member passage 14 and through coaxial passage 49 of cannula 33. Compression member 15 is approximately 200 cm in length and includes a 0.018 inch stainless steel wire about the proximal 100 cm thereof. The distal portion of the compression member comprises a 0.010 inch monofilament stainless steel wire that is soldered in a well-known manner with the aid of a cannula to the 0.018 inch proximal portion wire.

Although inner member tube 11 and outer member tube 16 have been described as an elastic material of preferably polytetrafluoroethylene, the elastic material of these elongated members can include at least one from a group consisting of polyfluoroethylenepropylene, polyimide, polyamide, polypropylene, polyurethane, polyethylene, polyethylenetheralate, polyvinylchloride, and vinyl. In addition, outer member tube 16 can also include a metallic alloy tube or coil such as stainless steel or other alloys of biocompatible metals including, for example, platinum, gold, and silver. It is to be also noted that the spacing between the inner and outer member tubes afforded by cross-sectional area 20 of outer member passage 18 is varied based on the selection of the inner member material. The indicated dimensions provided for the inner and outer member tubes and the spacing therebetween are based on experiments with the aforementioned polytetrafluoroethylene material. The indicated dimensions and spacing of the inner and outer member tubes was also experimentally derived so as not to exceed the elastic limit of the inner member tube. Accordingly, the dimensions and spacing of the inner and outer member tubes, which use other materials and/or dimensions, must be selected so as not to exceed the elastic limit of the inner member.

Figure 4:
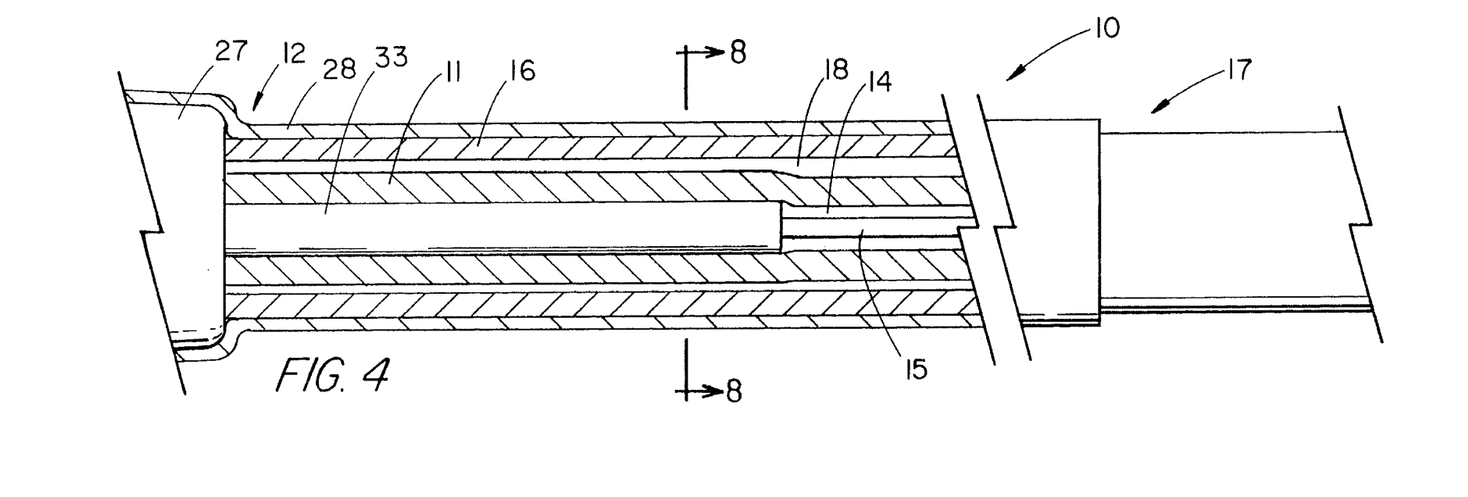
FIG. 4 depicts an enlarged, partially-sectioned view of another aspect of the cutting catheter of FIG. 2 proximate the interconnection of the inner member and the catheter handle hub.

FIG. 4 depicts an enlarged, partially-sectioned view of another aspect of cutting catheter 10 of FIG. 2 proximate the interconnection of inner member tube 11 and catheter handle hub 27. In this aspect, inner member 11 comprises a single lumen polytetrafluoroethylene material tube. Single lumen inner member tube 11 includes first passage 14 with hub cannula 33 and compression member wire 15 coaxially positioned therein as previously described.

Figures 8, 10:
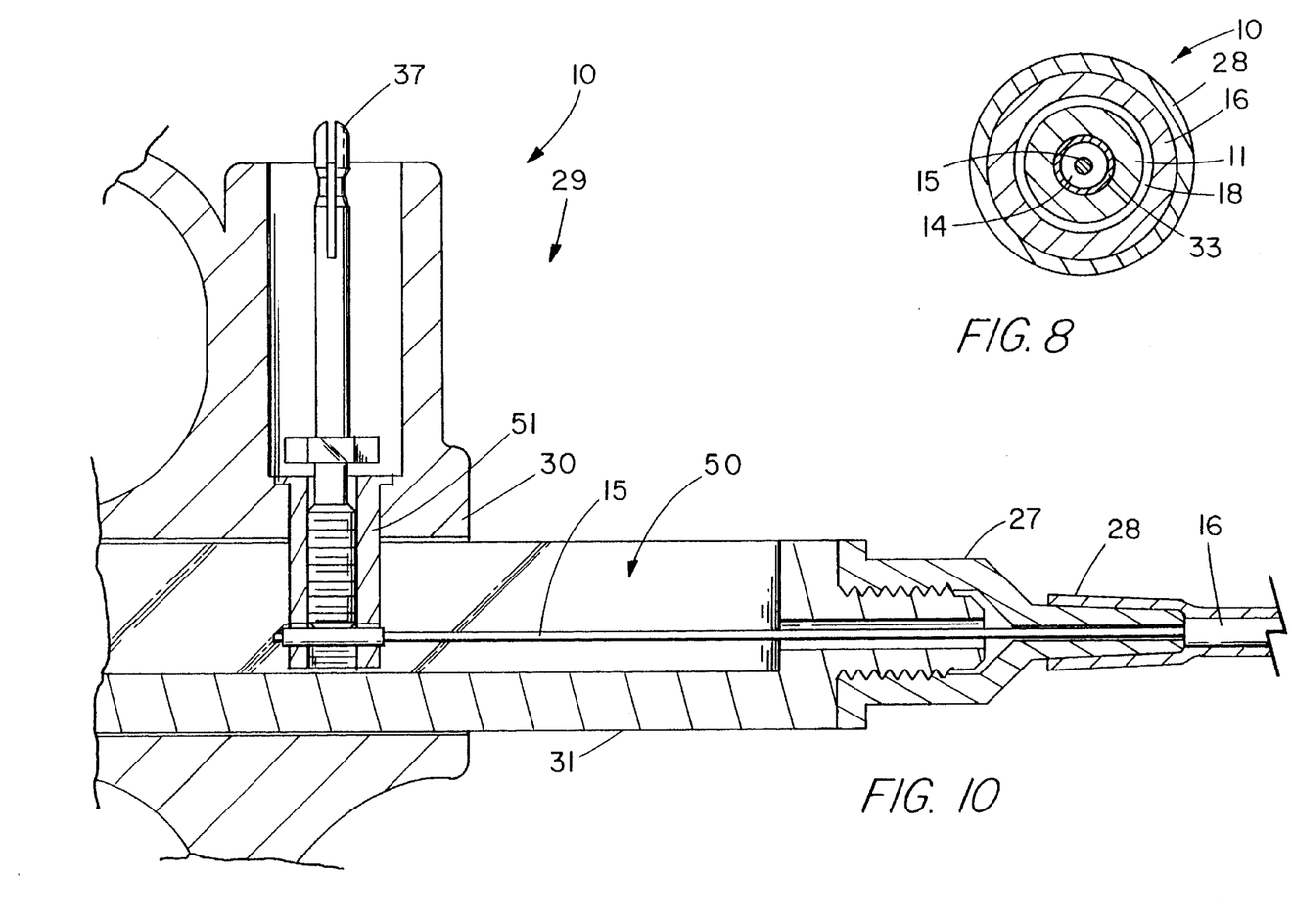
FIG. 8 depicts a cross-sectional view of the cutting catheter of FIG. 4 taken along the line 8—8.
FIG. 10 depicts an enlarged, partially sectioned view of a portion of the cutting catheter of FIG. 2 and, in particular, the distal portion of the handle and the distal ends of the outer member and the compression member.

FIG. 8 depicts a cross-sectional view of cutting catheter 10 of FIG. 4 taken along the line 8—8. Inner member tube 11 is coaxially positioned in outer member passage 18 with sufficient spacing between the inner and outer member tubes to allow for radial expansion of the inner member tube that is no greater than the elastic limit of the inner member tube.

As previously initially described, FIG. 5 depicts an enlarged, partially sectioned view of catheter 10 of FIG. 2 in the vicinity of side hub 24. Side hub 24 is a stainless steel Luer-lock hub in communication with second inner member passage 21 via angled, 18 gauge stainless steel cannula 25. Cannula 25 is approximately 2.5 cm in length with approximately 2.0 cm extending from side hub 24. Cannula 25 has an outside diameter of 0.047 inches and an inside diameter of 0.037 inches. As a result, the outside diameter of cannula 25 causes second inner member passage 21 to expand approximately 0.006 inches as shown. Outer member passage 18 includes elliptically-shaped side port 22 having a major diameter of approximately 0.254 inches. Similarly, second inner member passage 21 includes elliptically-shaped side port 23 having a major diameter of approximately 0.190 inches. Side ports 22 and 23 are positioned approximately 80 mm from the proximal ends of inner member tube 11 and outer member tube 16. Angled cannula 25 is positioned through side ports 22 and 23 and, as a result, at least partially attaches inner member tube 11 and outer member tube 16 thereat. Commercially available, polyolefin material heat shrink tube 26, approximately 3 cm in length, is positioned around outer member tube 16 and side hub 24, which positions them relative to each other. A 5 cm length of heat shrink tube 32 is positioned around heat shrink tube 26 and outer member tube 16 and is utilized to position a company logo thereon.

Figure 7:
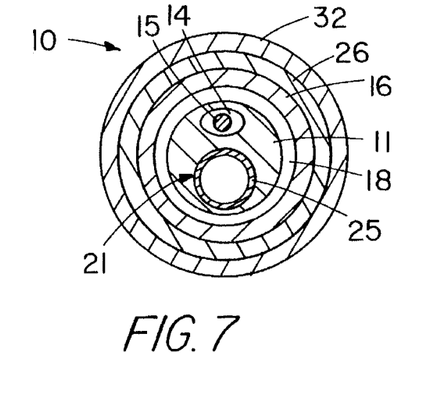
FIG. 7 depicts an enlarged, cross-sectional view of the cutting catheter of FIG. 5 taken along the line 7—7.

FIG. 7 depicts an enlarged, cross-sectional view of catheter 10 of FIG. 5 taken along the line 7—7. As similarly depicted in FIG. 6, inner member tube 11 is coaxially positioned in outer member passage 18. Compression member wire 15 is positioned in first inner member passage 14, whereas side hub cannula 25 is positioned in second inner member passage 21. As previously suggested, side hub cannula 25 expands second inner member passage 21 and somewhat distorts the cylindrical configuration of first inner member passage 14. In addition, the positioning of side hub cannula 25 in second inner member passage 21 causes partial contact and/or attachment between inner member tube 11 with outer member tube 16. This contact or at least partial attachment provides a fixed point at which radial expansion of inner member tube 11 occurs due to compression by compression member wire 15.

FIG. 10 depicts an enlarged, partially sectioned view of a portion of catheter 10 of FIG. 2 and, in particular, the distal portion of catheter handle 29 and the proximal ends of inner member tube 11, outer member tube 16, heat shrink tube 28, and compression member 15. Catheter handle hub 27 is threadably engaged with second handle part 31 with the proximal end of compression member wire 15 extending therethrough and into handle cavity 50. First handle part 30 includes electrical terminal 37 extending into cavity 50 and fixedly engaging the proximal end of compression member wire 15. Electrical terminal 37 is threadably engaged through electrical terminal socket 51 which is fixedly positioned in first handle part 30 using, for example, well-known ultrasound insertion techniques. First and second handle parts 30 and 31 are injection molded using, for example, commercially available plastic materials.

It is to be understood that the above-described cutting catheter is merely an illustrative embodiment of the principles of this invention and that other cutting catheters may be devised by those skilled in the art without departing from the spirit and scope of this invention. It is contemplated that various combinations of not yet specifically described materials and/or configurations of the inner and outer elongated members can be devised by those skilled in the art in practicing this invention. Regardless of the materials or configurations utilized, the spacing between the inner and outer members is paramount so that the radial expansion of the inner member does not exceed its elastic limit. Various points of full or partial attachment are also contemplated; however, the spacing between the inner and outer members still remains critical so as not to exceed the elastic limit of the inner member. Although this cutting catheter has been described for use in severing papilla or enlarging the duct in the papilla of Vater, this cutting catheter can also be used and positioned in the common bile duct through the papilla of Vater to obtain radiograms of the common bile duct. Contrast medium is injected through second inner member passage 18 and out the distal end of the cutting catheter. This procedure is commonly referred to as an endoscopic retrograde cholangiopancreatography.

What is claimed is:

1. A cutting catheter (10) comprising:

an inner, elongated member of an elastic material having a proximal end, a distal end, and a first passage extending longitudinally therein;

a compression member positioned in said first passage and attached to said inner member proximate said proximal end and distally therefrom, said compression member in a selected position longitudinally compressing and radially expanding said inner member proximate said proximal end to an elastic limit of said inner member; and an outer, elongated member having an inner passage extending therethrough, positioned around a proximal portion of said inner member, and a distal portion of said inner passage having a cross-sectional area in which said inner member can radially expand no greater than said elastic limit thereof, whereby the radial expansion of said inner member in said outer member is distributed longitudinally and distally from the attachment of said compression member to said inner member before said elastic limit of said inner member is reached.

2. The cutting catheter of claim 1 wherein said elastic material includes at least one from a group consisting of polytetrafluoroethylene, polyfluoroethylenepropylene, polyimide, polyamide, polypropylene, polyurethane, polyethylene, and polyethylenetheralate.

3. The cutting catheter of claim 1 wherein said outer member includes at least one material from a group consisting of polytetrafluoroethylene, vinyl, polyvinylchloride, polyimide, polypropylene, polyethylene, stainless steel, platinum, gold, and a metallic alloy.

4. The cutting catheter of claim 1 wherein said compression member comprises at least one from a group consisting of a wire, a tube, and a braid.

5. The cutting catheter of claim 1 wherein said inner member includes a second passage (21), wherein said inner passage of said outer member and said second passage of said inner member each includes a side port (22, 23) positioned distally of said proximal end of said inner member and in communication with each other and wherein said cutting catheter further includes a first hub (24) in communication with said second passage through said side ports.

6. The cutting catheter of claim 5 wherein said hub includes a cannula (25) positioned in said second passage through said side ports.

7. The cutting catheter of claim 6 further comprising a first heat shrink tube positioning said outer member and said first hub.

8. The cutting catheter of claim 7 further comprising a second hub proximate said distal end and in communication with said first passage of said inner member.

9. The cutting catheter of claim 8 further comprising a second heat shrink tube positioning said outer member and said second hub.

10. The cutting catheter of claim 1 further comprising a handle having first and second interconnected parts, wherein said first part is attached to said compression member and said second part is attached to said inner member.

11. The cutting catheter of claim 9 further comprising a hub proximate said distal end and in communication with said first passage of said inner member.

12. The cutting catheter of claim 11 wherein said hub includes a cannula.

13. The cutting catheter of claim 11 further comprising a heat shrink tube positioning said outer member and said hub.

14. A cutting catheter comprising:

an inner, flexible elongated member of an elastic material having a proximal end, a distal end, and a first and a second passage extending longitudinally therein;

a compression member positioned in said first passage and attached to said inner member proximate said proximal end and distally therefrom, said compression member in a selected position longitudinally compressing and radially expanding said inner member proximate said proximal end of said inner member to an elastic limit of said inner member; and an outer, elongated member having an inner passage extending therethrough and positioned around a proximal portion of said inner member, a distal portion of said inner passage having a cross-sectional area in which said inner member can radially expand no greater than said elastic limit thereof, whereby the radial expansion of said inner member in said outer member is distributed longitudinally and distally from the attachment of said compression member to said inner member before said elastic limit of said inner member is reached.

15. The cutting catheter of claim 14 wherein said second passage of said inner member and said inner passage of said outer member each includes a side port (22, 23) distal of said proximal end of said inner member and in communication with each other and wherein said cutting catheter further includes a first cannulated hub (24, 25) positioned in said second passage through said side ports.

16. The cutting catheter of claim 14 further comprising a first heat shrink tube positioning said outer member and said first cannulated hub.

17. The cutting catheter of claim 14 further comprising a second cannulated hub positioned in said first passage of said inner member at said distal end thereof.

18. The cutting catheter of claim 16 further comprising a second heat shrink tube positioning said outer member and said second cannulated hub.

19. The cutting catheter of claim 14 further comprising a handle having a first part attached to said compression member and a second part attached to said inner member.

20. The cutting catheter of claim 17 wherein said first passage is offset from a center line extending longitudinally through said inner member.

21. A papillotome comprising:

an inner, elongated member tube of polytetrafluoroethylene material having a proximal end, a distal end, and a first and a second passage extending longitudinally therein;

a stainless steel cannula positioned in said first passage and attached to said inner member tube proximate said proximal end and distally therefrom, said stainless steel cannula in an actuated position longitudinally compressing and radially expanding said inner member tube proximate said proximal end of said inner member tube to an elastic limit;

an outer, elongated member tube of said polytetrafluoroethylene material positioned around a proximal portion of said inner member tube and having an inner passage extending longitudinally therethrough, a distal portion of said inner passage having a cross-sectional area in which said inner member tube can radially expand no greater than said elastic limit;

a first hub having a cannula extending therefrom and positioned in said second passage of said inner member tube through a side port in said second passage of said inner member tube and a side port in said inner passage of said outer member tube;

a first heat shrink tube positioned around said outer member tube and said first hub;

a second hub having a cannula extending therefrom and positioned in said first passage of said inner member tube at said distal end thereof;

a second heat shrink tube positioned around said outer member tube and said second cannulated hub; and a handle having a second part attached to said second hub and a first part attached to said stainless steel cannula, whereby the radial expansion of said inner member tube in said outer member tube is distributed longitudinally and distally from the attachment of said stainless steel cannula to said inner member tube before said elastic limit of said inner member tube is reached.

* * * * *